United States Patent
Rabovsky et al.

(10) Patent No.: US 8,491,939 B2
(45) Date of Patent: Jul. 23, 2013

(54) ANTIOXIDANT DIETARY SUPPLEMENT COMPOSITIONS

(75) Inventors: Alexander B. Rabovsky, Idaho Falls, ID (US); Jeremy Ivie, Ammon, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 225 days.

(21) Appl. No.: 12/854,946

(22) Filed: Aug. 12, 2010

(65) Prior Publication Data

US 2011/0038967 A1 Feb. 17, 2011

Related U.S. Application Data

(60) Provisional application No. 61/233,247, filed on Aug. 12, 2009.

(51) Int. Cl.
*A61K 36/00* (2006.01)
*A23L 1/30* (2006.01)

(52) U.S. Cl.
USPC ............................ 424/725; 424/766; 426/648

(58) Field of Classification Search
USPC .................................. 424/725, 766; 426/648
See application file for complete search history.

(56) References Cited

U.S. PATENT DOCUMENTS

| | | |
|---|---|---|
| 7,628,984 B2 | 12/2009 | Prasad et al. |
| 8,017,147 B2 | 9/2011 | Mazed et al. |
| 2005/0095628 A1 | 5/2005 | Krempin et al. |
| 2007/0231371 A1 | 10/2007 | Pan et al. |
| 2009/0000734 A1 | 1/2009 | Ruhdorfer |

FOREIGN PATENT DOCUMENTS

| | | |
|---|---|---|
| WO | WO 01/19383 | 3/2001 |
| WO | WO 01/19383 A1 * | 3/2001 |
| WO | WO 2009/074644 | 6/2009 |

OTHER PUBLICATIONS

Rangaswamy et al. Lutein and Zeaxanthin in Leafy Greens and Their Bioavailability; Olive Oil Influences the Absorption of Dietary Lutein and Its Accumulation in Adult Rats; J. Agric. Food Chem. (2007) 55, pp. 6395-6400.*

AREDS report No. 9, "A randomized, placebo-controlled, clinical trial of high-dose supplementation with vitamins C and E and beta carotene for age-related cataract and vision loss," *Arch. Ophthalmol.,* 2001, 119:1439-1452.

Aust et al., "Supplementation with tomato-based products increases lycopene, phytofluene, and phytoene levels in human serum and protects against UV-light-induced erythema," *Int J Vitam Nutr Res.,* 2005, 75:54-60.

Basu and Imrhan, "Tomatoes versus lycopene in oxidative stress and carcinogenesis: conclusions from clinical trials," *Eur J Clin Nutr.,* 2007, 61:295-303.

Bohlke et al., "Vitamins A, C and E and the risk of breast cancer: results from a case-control study in Greece," *Br J Cancer,* 1999, 79:23-29.

Cherubini et al., "High vitamin E plasma levels and low low-density lipoprotein oxidation ore associated with the absence of atherosclerosis in octogenarians," *J Am Geriatr Soc.,* 2001, 49:651-654.

Cohn et al., "Comparative multiple dose plasma kinetics of lycopene administered in tomato juice, tomato soup or lycopene tablets," *Eur J Nutr.,* 2004, 43:304-312.

(Continued)

*Primary Examiner* — Patricia Leith
(74) *Attorney, Agent, or Firm* — Fish & Richardson P.C.

(57) ABSTRACT

This document provides dietary supplements. For example, compositions having a combination of ingredients useful in providing a broad scope of antioxidant protection for human or animal consumption are provided.

4 Claims, 2 Drawing Sheets

OTHER PUBLICATIONS

Coimbra et al., "The action of red wine and purple grape juice on vascular reactivity is independent of plasma lipids in hypercholesterolemic patients," *Braz J Med Biol Res.*, 2005, 38:1339-1347.

Conti et al., "Protective activity of silipide on liver damage in rodents," *Jpn J Pharmacol.*, 1992, 60:315-321.

Davi et al., "In vivo formation of 8-iso-prostaglandin f2alpha and platelet activation in diabetes mellitus: effects of improved metabolic control and vitamin E supplementation," *Circulation* 1999, 99:224-229.

de Lange et al., "Polyphenolic grape extract inhibits platelet activation through PECAM-1: an explanation for the French paradox," *Alcohol Clin Exp Res.*, 2007, 31:1308-1314.

Di Castelnuovo et al., "Meta-analysis of wine and beer consumption in relation to vascular risk," *Circulation*, 2002, 105:2836-2844.

Dorgan et al., "Relationships of serum carotenoids, retinal, alpha-tocopherol, and selenium with breast cancer risk: results from a prospective study in Columbia, Missouri (United States) ," *Cancer Causes & Control*, 1998, 9:89-97.

Enstrom et al., "Vitamin C intake and mortality among a sample of the United States population," *Epidemiology*, 1992, 3:194-202.

Enstrom, "Counterpoint-vitamin C and mortality," *Nutr Today*, 1993, 39-42.

Facino et al., "Diet enriched with procyanidins enhances antioxidant activity and reduces myocardial post-ischaemic damage in rats," *Life Sci.*, 1999, 64:627-642.

Ferrieres, [Nutritional epidemiology of coronary disease]. (article in French) *Arch Mal Coeur Vaiss*, 2003, 96(6):13-19.

Ferrieres, "The French paradox: lessons for other countries," *Heart*, 2004, 90:107-111.

Gale et al., "Antioxidant vitamin status and carotid atherosclerosis in the elderly," *Am J Clin Nutr.*, 2001, 74:402-408.

Gale et al., "Plasma antioxidant vitamins and carotenaids and age-related cataract," *Ophthalmology*, 2001, 108:1992-1998.

Giovannucci et al., "Intake of carotenoids and retinal in relation to risk of prostate cancer," *J Natl Cancer Inst.*, 1995, 87:1767-1776.

Han and Meydani, "Vitamin E and infectious diseases in the aged," *Proc Nutr Soc.*, 1999, 58:697-705.

Jacob et al., Influence of lycopene and vitamin C from tomato juice on biomarkers of oxidative stress and inflammation, *Br J Nutr.*, 2008, 99:137-146.

Keevil et al., "Grape juice, but not orange juice or grapefruit juice, inhibits human platelet aggregation," *J Nutr.*, 2000, 130:53-56.

Kiokias and Gordon, "Dietary supplementation with a natural carotenoid mixture decreases oxidative stress," *Eur J Clin Nutr.*, 2003;57:1135-1140.

Knoops et al., "Mediterranean diet, lifestyle factors, and 10-year mortality in elderly European men and women: the HALE project," *JAMA*, 2004, 292:1433-1439.

Kucuk et al., "Effects of lycopene supplementation in patients with localized prostate cancer," *Exp Biol Med.*, 2002, 227:881-885.

Losonczy et al., "Vitamin E and vitamin C supplement use and risk of all-cause and coronary heart disease mortality in older persons: the Established Populations far Epidemiologic Studies of the Elderly" *Am J Clin Nutr.*, 1996, 64:190-196.

Malafa et al., "Inhibition of angiogenesis and promotion of melanoma dormancy by vitamin E succinate," *Ann Surg Oncol.*, 2002, 9:1023-1032.

McCullough et al., "The effect of vitamin A on epithelial integrity," *Proc Nutr Sac.*, 1999, 58:289-293.

Morazzoni et al., "Comparative bioavailability of Silipide a new flavanolignan complex, in rats," *Eur J Drug Metob Pharmacokinet*, 1992, 17:39-44.

Osganian et al., "Vitamin C and risk of coronary heart disease in women," *J Am Coil Cardiol.*, 2003, 42:246-252.

Purba et al., "Skin wrinkling: can food make a difference?" *J Am Coil Nutr.*, 2001, 20:71-80.

Rabovsky and Cuomo, "Olive Oil: Direct Measure of Antioxidant Activity," *Free Radical Biology & Medicine*, 1999, 27:542 (abstr).

Rafi et al., "Lycopene inhibits LPS-induced proinflammatory mediator inducible nitric oxide synthase in mouse macrophage cells," *J Food Sci.*, 2007, 72:5069-5074.

Rao, "Processed tomato products as a source of dietary lycopene: bioavailabillty and antioxidant properties," *Can J Diet Pract Res.*, 2004, 65:161-165.

Ruano et al., "Phenolic content of virgin olive oil improves ischemic reactive hyperemia in hypercholesterolemic patients," *J Am Coil Cardiol.*, 2005, 46:1864-1868.

Russell, "The vitamin A spectrum: from deficiency to toxicity," *Am J Clin Nutr.*, 2000, 71:878-884.

Scalbert and Wilfiamson, "Dietary intake and bioavailability of polyphenols," *Journal of Nutrition*, 2000, 130:2073S-2085S.

Schwarz et al., "Lycopene inhibits disease progression in patients with benign prostate hyperplasia," *J Nutr.*, 2008, 138:49-53.

Shekelle et al., "Effect of supplemental vitamin E for the prevention and treatment of cardiovascular disease," *J Gen Intern Med.*, 2004, 19:380-389.

Simon and Hudes, "Serum ascorbic acid and gallbladder disease prevalence among US adults: the Third National Health and Nutrition Examination Survey (NHANE5 III)," *Arch Intern Med.*, 2000, 160:931-936.

Solomons, "Vitamin A and carotenoids," In: *Present Knowledge in Nutrition*, 2001, Bowman and Russell, eds., Washington D.C., ILSI Press, pp. 127-145.

Stahl et al., "Dietary tomato paste protects against ultraviolet light-induced erythema in humans," *J Nutr.*, 2001, 131:1449-1451.

Stampfer et al., "Vitamin E consumption and the risk of coronary disease in women," *N Engl J Med.*, 1993, 328:1444-1449.

Suharno et al., "Supplementation with vitamin A and iron for nutritional anaemia in pregnant women in West Java, Indonesia," *Lancet*, 1993, 342:1325-1328.

Thurnham and Northrop-Clewes, "Optimal nutrition: vitamin A and the carotenoids," *Proc Nutr Soc.*, 1999, 58:449-457.

Tyssandier et al., "Effect of tomato product consumption on the plasma status of antioxidant microconstituents and on the plasma total antioxidant capacity in healthy subjects," *J Am Coll Nutr.*, 2004, 23:148-156.

Ursini and Sevanian, "Wine polyphenols and optimal nutrition," *Ann N Y Acad Sci.*, 2002, 957:200-2009.

Ursini et al., "Optimization of nutrition: polyphenols and vascular protection," *Nutr Rev.*, 1999, 57:241-249.

Vigna et al., "Effect of a standardized grape seed extract on low-density lipoprotein susceptibility to oxidation in heavy smokers," *Metabolism*, 2003, 52:1250-1257.

Visioli et al., "Olive phenol hydroxytyrosol prevents passive smoking-induced oxidative stress," *Circulation*, 2000, 102:2169-2171.

Yusuf et al., "Vitamin E supplementation and cardiovascular events in high-risk patients. The Heart Outcomes Prevention Evaluation Study Investigators," *N Engl J Med.*, 2000, 342:154-160.

Zhang et al., "Dietary carotenoids and vitamins A, C, and E and risk of breast cancer," *J Natl Cancer Inst.*, 1999, 91:547-556.

Authorized Officer Joo-Hyung Heo, International Search Report in PCT/US2010/045271, mailed Apr. 25, 2011, 2 pages.

International Report on Patentability in PCT/US2010/045271, mailed Feb. 14, 2012, 4 pages.

* cited by examiner

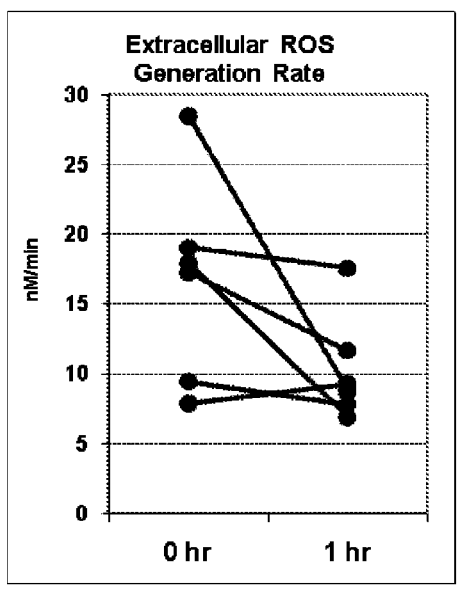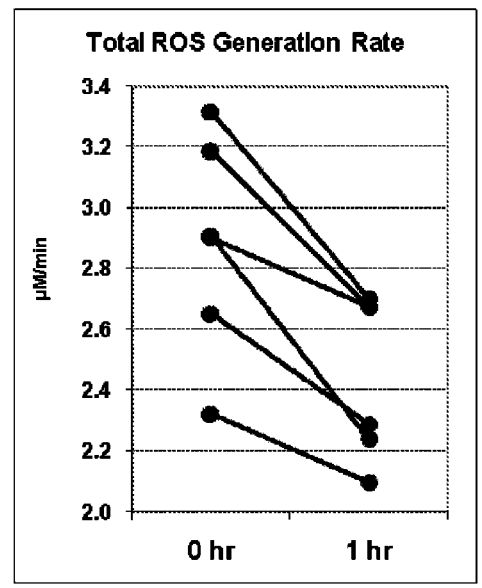
FIG. 2A
FIG. 2B

ANTIOXIDANT DIETARY SUPPLEMENT COMPOSITIONS

CROSS-REFERENCE TO RELATED APPLICATIONS

This application claims priority under 35 U.S.C. §119(e) to U.S. Provisional Application Ser. No. 61/233,247, filed on Aug. 12, 2009, which is incorporated by reference in its entirety herein.

BACKGROUND

1. Technical Field

This document relates to the field of dietary supplements. For example, this document relates to combinations of ingredients useful in providing a broad scope of antioxidant protection for human or animal consumption.

2. Background Information

Aging is a syndrome of changes that are deleterious, progressive, universal and thus far irreversible. It is believed that aging damage (deterioration) occurs to molecules (DNA, proteins, lipids) and that this molecular damage contributes to many diseases of old age. Examples of diseases which increase in frequency with age include arthritis, osteoporosis, heart disease, cancer, Alzheimer's Disease, etc. While such diseases are often associated with aging, such diseases can be distinguished from aging per se.

One of the most popular theories of aging is the "Free Radical Theory of Aging." This theory postulates that aging results from an accumulation of changes caused by reactions in the body initiated by highly reactive molecules known as "free radicals." The changes induced by free radicals are believed to be a major cause of aging and disease development.

More particularly, it is believed that free radical damage to DNA may lead to gene mutations that in turn increase the prevalence of cancer. Similarly, free radical damage to lipid molecules may cause LDL peroxidation, foam cells formation, and initiation of arterial plaque, which in turn can lead to the diseases of atherosclerosis and heart disease. As yet another example, free radical damage to protein molecules is believed to cause cross linking, amyloid formation, and brain cell alteration which in turn may cause or increase the incidence of Alzheimer's disease. Free radical damage to protein molecules may also cause tissue structure alteration and auto-immune disorders that lead to arthritis and as well as connective tissue damage (collagen, elastin, etc.) that affect skin function and appearance.

SUMMARY

This document provides dietary supplements. For example, this document provides composition having a combination of ingredients useful in providing a broad scope of antioxidant protection for human or animal consumption.

In one aspect, this document features a dietary supplement comprising, or consisting essentially of, (a) from about 5 mg to about 150 mg α-Tocopherol, (b) from about 0.7 mg to about 20 mg β-Tocopherol, (c) from about 10 mg to about 300 mg γ-Tocopherol, (d) from about 2.5 mg to about 75 mg δ-Tocopherol, (e) from about 0.01 mg to about 0.3 mg α-Carotene, (f) from about 0.2 mg to about 6 mg β-Carotene, (g) from about 0.02 mg to about 0.6 mg Criptoxanthin, (h) from about 0.01 mg to about 0.3 mg Zeaxanthin, (i) from about 0.01 mg to about 0.3 mg Lutein, (j) from about 0.3 mg to about 9 mg Lycopene, (k) from about 15 mg to about 450 mg Olive fruit extract, (l) from about 2.5 mg to about 75 mg Grape seed extract; and (m) from about 30 mg to about 900 mg Vitamin C. In some cases, the dietary supplement can comprise, or consist essentially of, (a) from about 40 mg to about 75 mg α-Tocopherol, (b) from about 5 mg to about 10 mg β-Tocopherol, (c) from about 80 mg to about 150 mg γ-Tocopherol, (d) from about 20 mg to about 40 mg δ-Tocopherol, (e) from about 0.08 mg to about 0.15 mg α-Carotene, (f) from about 1.5 mg to about 3 mg β-Carotene, (g) from about 0.15 mg to about 0.3 mg Criptoxanthin, (h) from about 0.08 mg to about 0.15 mg Zeaxanthin, (i) from about 0.08 mg to about 0.15 mg Lutein, (j) from about 2.5 mg to about 4.5 mg Lycopene, (k) from about 120 mg to about 225 mg Olive fruit extract, (l) from about 20 mg to about 40 mg Grape seed extract; and (m) from about 240 mg to about 450 mg Vitamin C. In some cases, the dietary supplement can comprise, or consist of, (a) about 50 mg α-Tocopherol, (b) about 6.6 mg β-Tocopherol, (c) about 100 mg γ-Tocopherol, (d) about 25 mg δ-Tocopherol, (e) about 0.1 mg α-Carotene, (f) about 2 mg β-Carotene, (g) about 0.2 mg Criptoxanthin, (h) about 0.1 mg Zeaxanthin, (i) about 0.1 mg Lutein, (j) about 3 mg Lycopene, (k) about 150 mg Olive fruit extract, (l) about 25 mg Grape seed extract; and (m) about 300 mg Vitamin C.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 2A and 2B are line graphs of the change in extracellular and total ROS, respectively, following administration of a dietary supplement formulation as described herein.

DETAILED DESCRIPTION

Figure 1:
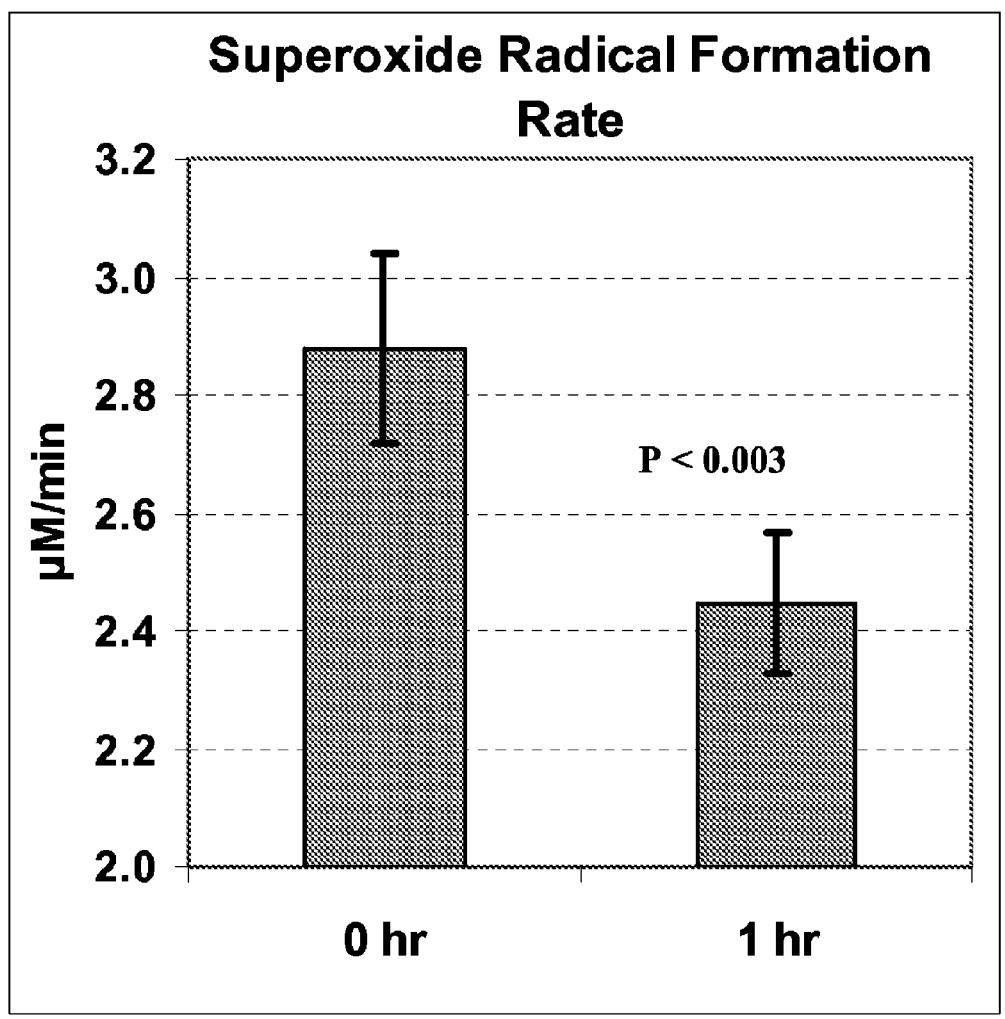
FIG. 1 is a bar graph showing the rate of free radical generation before and after administration of a dietary supplement described herein.

In the following description, numerous specific details are set forth in order to provide a thorough understanding of the present document. It will be obvious, however, to one skilled in the art that the subject matter provided herein may be practiced without these specific details. In other instances, well-known aspects of dietary supplements and the various compositions discussed herein have not been described in particular detail in order to avoid unnecessarily obscuring the subject matter provided herein.

Provided herein are dietary supplement formulations that provide superior broad-spectrum anti-aging and anti-oxidant protection at the cellular level that may block or slowdown damaging of DNA, lipid and protein molecules. The superior broad-spectrum anti-aging and anti-oxidant blend can protect many classes of bio-molecules involved in the aging process from damage. In some embodiments, a dietary supplement formulation provided herein can include fat-soluble antioxidants, phenolic compounds, and/or water soluble antioxidants.

The antioxidant compositions provided herein can be designed to mirror the Mediterranean diet, which is widely regarded for its health benefits. Ingredients of the Mediterranean diet can include red wine, tomatoes, and olive oil. In some cases, a dietary supplement formulation provided herein can include lycopene (e.g., tomatoes), olive fruit extract, grape seed extract, tocopherols (e.g., olive oils), carotenoids (e.g., vegetables, green and red), and/or Vitamin C (e.g., fruit). By providing a broad mix of antioxidant compounds that penetrate different areas of cells, plasma, tissue, and organs, this document synergistically provides for broad spectrum antioxidant compositions.

It is believed that such a broad spectrum antioxidant product will provide various health benefits such as: decrease in skin sensitivity to UV irradiation, improvement of oxidative status in healthy volunteers, protection from epidermal permeability barrier, prevention of wrinkle formation, and reduction or prevention of cellular damage.

One component of the compositions provided herein can be fat-soluble antioxidants. Fat-soluble antioxidants are cell membrane, tissue, and lipoprotein protecting antioxidants which are preferably found in heavy concentrations in cellular membranes and skin. These compounds act as an internal sunscreen to absorb free radicals and protect against sun damage and environmental aging. They also aid in protection of free radical DNA damage in all cells.

A first class of fat-soluble antioxidants includes tocopherols such as α-Tocopherol, β-Tocopherol, γ-Tocopherol, and δ-Tocopherol. These tocopherols can reduce the risk of cardiovascular disease, reduce the risk of cataracts, and improve immune system function.

Another class of fat-soluble antioxidants for use in the disclosed compositions are mixed carotenoids. One mixed carotenoid blend includes: α,β-Carotene, Criptoxanthin, Zeaxanthin, Lutein, and Lycopene. Expected or potential benefits of such compounds include: improved vision (eye) function, improved regulation of gene expression, improved immune system function, improved body and organ growth and development, improved red blood cell production, decreased lipid peroxidation markers, increasing resistance of LDL to oxidation, decreasing DNA peroxidation markers, decreased inflammation, reduced UV-light induced skin erythema, reduced risk of prostate cancer, and reduced risk of breast cancer.

Lycopene is a pigment that gives vegetables and fruits, such as tomatoes, pink grapefruit and watermelon, their red color. It also appears to have strong antioxidant capabilities. Several studies and research suggest that consumption of foods rich in lycopene is associated with a lower risk of prostate cancer and cardiovascular disease. Lycopene is believed to provide benefits such as: decreasing lipid peroxidation markers, increasing resistance of LDL to oxidation, decreasing DNA peroxidation markers, decreasing inflammation, reducing UV-light induced skin erythema, reducing risk of prostate cancer, and reducing risk of breast cancer.

Lycopene is a carotenoid, fat soluble substance. Because of this, solubility is often an issue. Lycopene is an example of the situation when active ingredient is poorly bioavailable from natural source, but can be improved as a supplement in highly processed food. The reason of this is location of Lycopene in nuclear chromatin, which is not easy to digest. High temperatures and presence of oil (frying, cooking) are conditions of Lycopene extraction, as are the methods used to prepare Lycopene for dietary supplement consumption.

Another component of composition provided herein is phenolic compounds. Such phenolic compounds can be involved with activating a liver detoxification response, anti inflammation properties, and reduction in the generation of free radicals in plasma, organs, and tissue. A first class of phenolic compounds includes an olive extract. Tyrosol, Hydroxytyrosol, and Verbascoside, along with different combination of theirs derivatives, are representative of olive phenolic compounds Olive extract can provide a number of health benefits that potentially include: directing antioxidant activity, decreasing oxidative stress markers, reducing risk of cardiovascular disease, reducing risk of cancer, decreasing inflammation, and decreasing wrinkles.

Symbol of the Mediterranean culture, the olive tree has gained interest for its superb properties of various kinds The tree, in fact, is extremely long living, and this is also due to its content of potent antioxidant compounds. Recently, the beneficial health properties of olive oil and fruit consumption have been correlated to a decreased incidence of various diseases in the Mediterranean area, as long-term consumption of a Mediterranean-type diet is associated with a lower incidence of cardiovascular and other free-radical mediated diseases.

Olive polyphenols exert a free radical scavenging activity that has a direct impact on skin health, as they prevent oxidative damage related to wrinkle formation, skin thinning, dehydration, etc. The scavenging and anti-inflammatory ability of olive polyphenols appear to be one of the treatments of choice for skin care in terms of wrinkles and aging prevention.

Another class of phenolic compounds that can be used as described herein is grape seed extract. Grape seed extract is believed to provide a number of health benefits that potentially include: directing antioxidant activity, metal chelating, effects on cell-signaling pathways, stimulating phase II detoxification enzyme activity, inhibiting proliferation and inducing apoptosis, inhibiting tumor invasion and angiogenesis, and decreasing inflammation.

Grape seed extracts include small molecular size polyphenols, named oligomeric proanthocyanidins. Grape seed extracts can have variable chemical compositions and polyphenols, which are known for their low and erratic bio-availability. The role of polyphenols in human nutrition is discussed on the basis of their redox chemistry, which accounts for the observed antioxidant effect and in turn for their protective effect against atherosclerosis.

Another component of a composition provided herein is a water soluble antioxidant compound. A preferred water soluble antioxidant compound is Vitamin C (ascorbic acid). Vitamin C is an essential nutrient found mainly in fruits and vegetables. The body requires it to form and maintain bones, blood vessels, and skin. Vitamin C is believed to be very bio-available, working in blood plasma and penetrating into cells. It is believed that Vitamin C provides many health benefits, including: decreasing oxidative stress markers, direct antioxidant activity, reducing risk of CVD, reducing risk of stroke, reducing risk of cancer, reducing UV-light induced skin erythema, and reducing risk of cataracts.

In some cases, a composition provided herein can include one or more of: α-Tocopherol, β-Tocopherol, γ-Tocopherol, δ-Tocopherol, α,β-Carotene, Criptoxanthin, Zeaxanthin, Lutein, Lycopene, Olive fruit extract, Grape seed extract, and Vitamin C.

In one case, a daily dosage of the composition includes:
a) from about 5 mg to about 150 mg α-Tocopherol;

b) from about 0.7 mg to about 20 mg β-Tocopherol;
c) from about 10 mg to about 300 mg γ-Tocopherol;
d) from about 2.5 mg to about 75 mg δ-Tocopherol;
e) from about 0.01 mg to about 0.3 mg α-Carotene;
f) from about 0.2 mg to about 6 mg β-Carotene;
g) from about 0.02 mg to about 0.6 mg Criptoxanthin;
h) from about 0.01 mg to about 0.3 mg Zeaxanthin;
i) from about 0.01 mg to about 0.3 mg Lutein;
j) from about 0.3 mg to about 9 mg Lycopene;
k) from about 15 mg to about 450 mg Olive fruit extract (10% total phenolic content by weight);
l) from about 2.5 mg to about 75 mg Grape seed extract; and
m) from about 30 mg to about 900 mg Vitamin C.

In another case, a daily dosage of the composition includes:
a) from about 25 mg to about 100 mg α-Tocopherol;
b) from about 3.5 mg to about 13 mg β-Tocopherol;
c) from about 50 mg to about 200 mg γ-Tocopherol;
d) from about 12 mg to about 50 mg δ-Tocopherol;
e) from about 0.05 mg to about 0.2 mg α-Carotene;
f) from about 1 mg to about 4 mg β-Carotene;
g) from about 0.1 mg to about 0.4 mg Criptoxanthin;
h) from about 0.05 mg to about 0.2 mg Zeaxanthin;
i) from about 0.05 mg to about 0.2 mg Lutein;
j) from about 1.5 mg to about 6 mg Lycopene;
k) from about 75 mg to about 300 mg Olive fruit extract (10% total phenolic content by weight);
l) from about 12 mg to about 50 mg Grape seed extract; and
m) from about 150 mg to about 600 mg Vitamin C.

In still another case, a daily dosage of the composition includes:
a) from about 40 mg to about 75 mg α-Tocopherol;
b) from about 5 mg to about 10 mg β-Tocopherol;
c) from about 80 mg to about 150 mg γ-Tocopherol;
d) from about 20 mg to about 40 mg δ-Tocopherol;
e) from about 0.08 mg to about 0.15 mg α-Carotene;
f) from about 1.5 mg to about 3 mg β-Carotene;
g) from about 0.15 mg to about 0.3 mg Criptoxanthin;
h) from about 0.08 mg to about 0.15 mg Zeaxanthin;
i) from about 0.08 mg to about 0.15 mg Lutein;
j) from about 2.5 mg to about 4.5 mg Lycopene;
k) from about 120 mg to about 225 mg Olive fruit extract (10% total phenolic content by weight);
l) from about 20 mg to about 40 mg Grape seed extract; and
m) from about 240 mg to about 450 mg Vitamin C.

A total daily dose may be prepared and administered in the form of one or more tablets (e.g., two tablets, three tablets, four tablets, five tablets, and six tablets). In some cases, the one or more tablets can be administered in one or more dosages over the course of 24 hours (e.g., one dose, two doses, three doses, four doses, five doses, and six doses), wherein the one or more dosages do not exceed the total daily dose.

A dietary supplement composition provided herein can be provided in any suitable dosage form, the selection and implementation of which will be apparent to those skilled in the art in view of the disclosure herein. Examples of such dosage forms include: a liquid, a gel, a tablet, a capsule, a powder, a confectionary, a shake, a bar, and a supplemented food. The selection and use of suitable excipients, flavorings, colorants, and the like will be apparent to those skilled in the art in view of the disclosure herein.

The following examples are intended to illustrate but not limit the invention.

EXAMPLES

Example 1

A Dietary Supplement Formulation

A dietary supplement formulation was prepared using by combining the components listed below in Table 1 with appropriate excipients. The combined formulation was then pressed into tablets (the daily dosage provided in Table 1 represents the amount in two tablets).

TABLE 1

| | Daily Dosage |
|---|---|
| α-Tocopherol | 50 mg |
| β-Tocopherol | 6.6 mg |
| γ-Tocopherol | 100 mg |
| δ-Tocopherol | 25 mg |
| α-Carotene | 0.1 mg |
| β-Carotene | 2 mg |
| Criptoxanthin | 0.2 mg |
| Zeaxanthin | 0.1 mg |
| Lutein | 0.1 mg |
| Lycopene | 3 mg |
| Olive fruit extract | 150 mg |
| Grape seed extract | 25 mg |
| Vitamin C | 300 mg |

Example 2

Rate of Free Radical Formation

EPR spin-trapping technology was used to measure the rate of free radicals formation circulating in human blood. For the test, several samples of human blood were mixed with different individual ingredients and tested by EPR spin-trapping technology to determine the rate of free radical generation. Preliminary data showed that some of the ingredients decreased the rate of free radical generation, while others increased this parameter. Thus, the method gives a possibility to compare properties of potential supplements in vitro.

Example 3

Reduction in the Rate of Free Radical Generation

A dietary supplement formula was prepared as described in Example 1 above. The dietary supplement composition was tested on six volunteers. Volunteers reported to the Lab in the morning fasting (last meal was 10-12 hour prior experiment). The daily dose of 2 tablets was taken with water. One drop of blood was taken from each volunteer before supplementation and one hour after supplementation. Samples were transferred to the EPR instrument used in Example 2 for measuring rate of free radical formation. The samples were tested and FIG. 1 shows the determined rate of free radical generation.

As can be seen in FIG. 1, the rate of free radical generation was significantly less after the tablets were administered each participant (15% on average).

Example 4

In vivo Antioxidant Study

The in vivo antioxidant effect of the formulation of Example 1 was evaluated in a human clinical experiment. In this study, six healthy volunteers were given a daily dose of the formulation.

Free radical (Reactive Oxygen Species—ROS) generation rate was measured in a blood sample from each volunteer before and 1 hour after supplementation. A known method of measuring ROS in circulating blood was used. Briefly, 20 µL of freshly taken capillary blood was mixed with the same volume of KREBS-HEPES buffer, pH—7.4, containing a spin label. To measure +Total ROS, the membrane-penetrable label CMH (1-hydroxy-3-methoxycarbonyl-2,2,5,5-tetramethylpyrrolidine) was used as the spin label at the final concentration of 400 µM. Extracellular ROS was measured using membrane-non-penetrable label PPH (1-hydroxy-4-phosphono-oxy-2,2,6,6-tetramethyl-piperidine) as the spin label at the concentration of 1000 µM.

Measurements were taken using a Bench-Top EPR spectrometer E-SCAN (Noxygen GmbH) and ELEXSYS EPR spectrometer (Bruker BioSpin GmbH). EPR parameters were as follows: center field: g=2.011, sweep width: 60 G, frequency: 9.76 GHz, power: 20 mW, gain: $1.00 \times 10^3$, modulation amplitude: 2.2 G, sweep time: 5.24 sec, number of scans: 10. Total ROS generation rate was statistically significant decreased on average 15.0±2.3% ($p<0.001$). As shown in FIG. 2, the extracellular level of ROS generation exhibited a statistically significant decrease of an average of 28±13% ($p<0.001$).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A dietary supplement, comprising:
 a) from about 5 mg to about 150 mg α-Tocopherol;
 b) from about 0.7 mg to about 20 mg β-Tocopherol;
 c) from about 10 mg to about 300mg γ-Tocopherol;
 d) from about 2.5 mg to about 75 mg δ-Tocopherol;
 e) from about 0.01 mg to about 0.3 mg α-Carotene;
 f) from about 0.2 mg to about 6 mg β-Carotene;
 g) from about 0.02 mg to about 0.6 mg Criptoxanthin;
 h) from about 0.01 mg to about 0.3 mg Zeaxanthin;
 i) from about 0.01 mg to about 0.3 mg Lutein;
 j) from about 0.3 mg to about 9 mg Lycopene;
 k) from about 15 mg to about 450 mg Olive fruit extract;
 l) from about 2.5 mg to about 75 mg Grape seed extract; and
 m) from about 30 mg to about 900 mg Vitamin C.

2. The dietary supplement of claim 1, comprising:
 a) from about 40 mg to about 75 mg α-Tocopherol;
 b) from about 5 mg to about 10 mg β-Tocopherol;
 c) from about 80 mg to about 150mg γ-Tocopherol;
 d) from about 20 mg to about 40 mg δ-Tocopherol;
 e) from about 0.08 mg to about 0.15 mg α-Carotene;
 f) from about 1.5 mg to about 3 mg β-Carotene;
 g) from about 0.15 mg to about 0.3 mg Criptoxanthin;
 h) from about 0.08 mg to about 0.15 mg Zeaxanthin;
 i) from about 0.08 mg to about 0.15 mg Lutein;
 j) from about 2.5 mg to about 4.5 mg Lycopene;
 k) from about 120 mg to about 225 mg Olive fruit extract;
 l) from about 20 mg to about 40 mg Grape seed extract; and
 m) from about 240 mg to about 450 mg Vitamin C.

3. The dietary supplement of claim 1, comprising:
 a) about 50 mg α-Tocopherol;
 b) about 6.6 mg β-Tocopherol;
 c) about 100 mg γ-Tocopherol;
 d) about 25 mg δ-Tocopherol;
 e) about 0.1 mg α-Carotene;
 f) about 2 mg β-Carotene;
 g) about 0.2 mg Criptoxanthin;
 h) about 0.1 mg Zeaxanthin;
 i) about 0.1 mg Lutein;
 j) about 3 mg Lycopene;
 k) about 150 mg Olive fruit extract;
 l) about 25 mg Grape seed extract; and
 m) about 300 mg Vitamin C.

4. The dietary supplement of claim 1, wherein the dietary supplement, when administered to a human, reduces a rate of free radical generation.

* * * * *

UNITED STATES PATENT AND TRADEMARK OFFICE
CERTIFICATE OF CORRECTION

PATENT NO. : 8,491,939 B2
APPLICATION NO. : 12/854946
DATED : July 23, 2013
INVENTOR(S) : Alexander B. Rabovsky Page 1 of 1

It is certified that error appears in the above-identified patent and that said Letters Patent is hereby corrected as shown below:

Title Page 2, Column 1 (Other Publications), line 33, please delete "carotenaids" and insert --carotenoids--, therefor;

Title Page 2, Column 2 (Other Publications), line 11, please delete "bioavailabillty" and insert --bioavailability--, therefor;

In the Claims

Column 8, line 1, in Claim 1, please delete "300mg" and insert --300 mg--, therefor;

Column 8, line 17 (approx.), in Claim 2, please delete "150mg" and insert --150 mg"--, therefor.

Signed and Sealed this
Twenty-ninth Day of October, 2013

Teresa Stanek Rea
*Deputy Director of the United States Patent and Trademark Office*